United States Patent [19]

Seaborne et al.

[11] Patent Number: 4,710,228

[45] Date of Patent: Dec. 1, 1987

[54] EDIBLE COATING COMPOSITION AND METHOD OF PREPARATION

[75] Inventors: Jonathan Seaborne, Corcoran; David C. Egberg, Plymouth, both of Minn.

[73] Assignee: General Mills, Inc., Minneapolis, Minn.

[21] Appl. No.: 788,178

[22] Filed: Oct. 16, 1985

[51] Int. Cl.[4] .......................... C08L 89/00; C09F 1/00; C08G 8/34

[52] U.S. Cl. .................................... 106/218; 106/219; 260/97; 426/89; 527/600; 527/601; 527/602; 527/604

[58] Field of Search .................. 260/97; 527/600, 602, 527/604, 601; 106/218, 219

[56] References Cited

U.S. PATENT DOCUMENTS

| | | | |
|---|---|---|---|
| 2,448,320 | 8/1948 | McIntosh | 106/218 |
| 2,811,453 | 10/1957 | Childs | 426/92 |
| 2,816,061 | 12/1957 | Doerr et al. | 424/34 |
| 2,909,434 | 2/1966 | Patten et al. | 426/125 |
| 2,951,763 | 4/1966 | Kelly et al. | 426/125 |
| 3,043,747 | 7/1962 | Long | 424/34 |
| 3,141,778 | 7/1964 | Thompson et al. | 426/125 |
| 3,145,111 | 3/1966 | Norton | 426/125 |
| 3,157,518 | 11/1964 | Battista | 99/171 |
| 3,248,232 | 4/1966 | Krajewski | 426/303 |
| 3,267,059 | 8/1966 | Cockeram | 527/601 |
| 3,323,922 | 6/1967 | Durst | 426/89 |
| 3,382,078 | 5/1968 | Melio et al. | 426/106 |
| 3,390,049 | 6/1968 | Rednick et al. | 424/34 |
| 3,471,303 | 10/1969 | Hamdy et al. | 426/89 |
| 3,560,222 | 2/1971 | Delaney | 426/652 |
| 3,576,663 | 4/1971 | Signorino et al. | 424/34 |
| 3,741,795 | 6/1973 | Signorino | 426/89 |
| 4,661,359 | 4/1987 | Seaborne et al. | 426/92 |

FOREIGN PATENT DOCUMENTS 942539 11/1963 United Kingdom .

OTHER PUBLICATIONS

"Dictionary of Food Ingredients", by Robert S. Igoe, Van Nostrand, Reinhold Co., 1983, pp. 69–70.

Primary Examiner—Theodore Morris
Attorney, Agent, or Firm—John A. O'Toole

[57] ABSTRACT

Disclosed are edible film coating compositions of low moisture permeability and their methods of preparation. The compositions comprise cross-linked, refined shellac and preferably an edible member having a reactive hydroxyl or acid moiety selected from the group consisting of edible sources of polyphenolics, edible sources of benzaldehyde and derivatives, acetylated monoglycerides, polyglycerol esters, edible straight chain monocarboxylic acid, edible di-carboxylic acids and mixtures thereof. Useful weight ratios of shellac to reactant range from 1:0.001 to 0.1. In the preferred method of preparation, the shellac is cross-linked with the reactants in a dry, molten mixture by heating at 130° to 175° C. for 2 to 15 minutes. The resulting coating compound while molten is dissolved in a food grade solvent, applied to a substrate and dried. The coating compositions are particularly useful as a moisture barrier in composite food articles having phases in contact which differ substantially in water activity. Effective films range fro 0.1 to 5 mils in thickness.

12 Claims, 1 Drawing Figure

TABLE IV

FILM COATING WATER RESISTANCE ON COATED CHOCOLATE CHIPS

| FILM COMPOSITION* | COATING LIFETIME (HOURS)** |
|---|---|
| | 6 24 48 72 96 120 144 168 192 216 240 264 288 312 336 360 384 400 432 456 |
| UNCOATED CHIP | F[A] |
| COATED BLEACHED SHELLAC | —F |
| EXAMPLE 5 | ————————————————————————————F |
| 6 | ——————————F |
| 7 | ————————————————————F |
| 8 | ——————————————————————F |
| 13 | ————————————————————————F |
| 14 | ——————————————————————————F |
| 16 | ————————————————————————F |
| 17 | ————————————————————————F |
| 20 | ——————————————————————————————F |

\* COATINGS AT 2% BY WEIGHT OF CHOCOLATE CHIP
\*\* TEST CONDITIONS: 36°F (2°C) AND SUSPENDED IN 0.97 Aw YOGURT
An "F" INDICATES COATING FAILURE I.E. CHIPS BEGIN TO BLEED IN MEDIA.

TABLE IV

FILM COATING WATER RESISTANCE ON COATED CHOCOLATE CHIPS

| FILM COMPOSITION* | COATING LIFETIME (HOURS)** |
|---|---|
| | 6 24 48 72 96 120 144 168 192 216 240 264 288 312 336 360 384 400 432 456 |
| UNCOATED CHIP | F^A |
| COATED BLEACHED SHELLAC | ———F |
| EXAMPLE 5 | ———————————————————————————————F |
| 6 | ———————————————————F |
| 7 | ——————————————————————————F |
| 8 | ———————————————————————————————F |
| 13 | ————————————————————————————————F |
| 14 | ————————————————————————————————F |
| 16 | ——————————————————————————————F |
| 17 | ——————————————————————————————F |
| 20 | —————————————————————————————————F |

\* COATINGS AT 2% BY WEIGHT OF CHOCOLATE CHIP

\*\* TEST CONDITIONS: 36°F (2°C) AND SUSPENDED IN 0.97 Aw YOGURT
An "F" INDICATES COATING FAILURE I.E. CHIPS BEGIN TO BLEED IN MEDIA.

EDIBLE COATING COMPOSITION AND METHOD OF PREPARATION

BACKGROUND OF THE INVENTION

1. Technical Field

The present invention relates to food products and to their methods of preparation. More particularly, the present invention relates to edible food coating compositions comprising cross-linked shellac and certain selected edible reactants and to their methods of preparation.

2. The Prior Art

Although the coating of food to protect such food against oxidative degradation, mold attack, and moisture penetration is well known, most coatings employed for such purposes are not edible and must be removed before the food can be consumed. If the coating employed adheres well to the the food product, the removal of such coating can be difficult and time consuming. Additionally, if the food product is brittle and fragile, the food product can break during the stripping of the coating, making the consumption of the food difficult and resulting in the loss of the food product. An edible food coating which does not require removal prior to consumption of the food product and which affords the necessary protection, particularly against moisture penetration, is therefore highly desirable.

A particular problem exists in the protection of food products with edible coatings or barriers with respect to composite foods comprising phases of dissimiliar materials, e.g., ice cream sandwiches or cheese and crackers, whose composite phases may differ in such properties as water activity, acidity, protein level and the like. Due to the various gradients in water activity and the like between the phases as well as the physical contact, migration and/or diffusion of species between the phases can occur which can result in degradation of the properties of each phase. For example, moisture may migrate from the cheese to the cracker undesirably drying the cheese and at the same time undesirably reducing the crispness of the cracker. Furthermore, removal of any intermediate barrier material can be quite inconvenient.

Among the various potential gradients in such composite food articles, moisture migration remains the most significant problem area. While throughout the remainder of the specification below, particular attention is addressed to the problems of moisture migration and moisture penetration of coating or barrier compositions, the skilled artisan will appreciate that the present invention also finds usefulness in the problems associated with additional migration or penetration problems including oxygen, acidity, color, oil and protein.

In the past, the art has attempted to prepare composite food articles by formulating the different food phases so that the water activity of the phases were approximately the same so as to minimize moisture migration. However, not only does this limit the range of composite food products possible, but moisture migration problems remain nonetheless. One approach towards providing an edible, low water permeable barrier has been to formulate barriers based upon compound fats (see U.S. Pat. No. 4,396,633, issued Aug. 2, 1983 to D. Tresser) or with formed in-situ gel membrane (see U.S. Pat. No. 4,401,681, issued Aug. 30, 1983 to Dahle). However, such barrier or coating compositions suffer from numerous disadvantages. Among the problems is that in order for compound fat coatings or barriers to be effective over long periods of time, the fat coats must be relatively thick. Additionally, especially with regard to chilled or frozen food articles, the fat barriers become relatively brittle at rhese reduced temperatures. Fissures or cracks may occur breaching the integrity of the barrier and allowing moisture migration to occur. Also, the fat coatings may be organoleptically undesirable providing a noticeable presence in an undesirably waxy mouthfeel especially at reduced consumption temperatures.

The prior art additionally includes attempts at providing edible coating compositions of low water permeability which are effective as relatively thin films. Coating compositions based upon modified methyl or ethyl cellulose ether are known (see U.S. Pat. No. 3,471,304 and U.S. Pat. No. 3,471,303, each issued Oct. 7, 1969 to M. M. Handy et al.). Additionally, coating compositions based upon shellac are also known (see U.S. Pat. No. 3,741,795, issued June 26, 1973 to C. A. Signorino). However, the compositions of each of these two references suffer from several disadvantages. First, each of the food compositions, while designated as edible, typically include ingredients which are not approved by the Food and Drug Administration. Additionally, while the coating compositions do provide a measure of water impermeability, further improvements in this important attribute are desirable. Also, the '304 patent teaches the necessity of employing both acylated fatty glycerides and certain metal salts.

This invention is suitable for commercial operations and provides compositions which have improved properties in the edible food coating fields. The compositions of the present invention may be prepared in the form of pre-polymerized or baked on films depending on the heat tolerance properties of the substrate coated. After air drying or curing the film possesses excellent oil, water and aging resistance and unusual toughness and elasticity or flexibility. Various other outstanding properties will be apparent from the following description of the compositions of the present invention disclosures.

When small molecules permeate through a polymer membrane, the rate of permeation can be expressed by parameters which may be characteristic of the polymer. The general concept of the ease with which a permeant passes through a barrier is often referred to as "permeability." This general term "permeability" does not refer to the mechanism of the permeation but only to the rate of the transmission or transport.

Membranes or films are generally described as permeable, semi-permeable (permeable to some substances but not to others), or perm-selective permeable to different extents to different molecular species under equal driving force. Consequently, a given membrane may be described by any one of these terms depending upon the nature of the penetrant or penetrants being studied (e.g., cellulose is permeable to water, perm-selective to water-glucose solutions and semi-permeable to water-protein solutions).

The terms permeability and permeability coefficient are defined in various ways by different authors, particularly when they are involved in different areas of research. The skilled artisan obtaining permeability information from the literature must therefore look carefully at the units of the permeability constants and the method of measurement. The permeability coefficient P is generally the proportionality constant between the flow of penetrant per unit area of membrane per unit time and the driving force per unit thickness of membrane. In the literature, however, one also finds flow per time, flow per area per time, or flow per area per time per unit thickness, all under the general term permeability. In the latter cases, the permeability coefficient may be an intrinsic property of the membrane, or it may be only a phenomenological property dependent on experimental conditions during measurements.

For purposes of illustration in Table 1 below, the permeability to water vapor or, synonymously, the water vapor permeability constants of a number of different non-edible polymer films are listed (as reported in "Permeability of Plastic Films and Coated Paper to Gases and Vapor," V. Stannett, et al., TAPPI Monograph Series No. 23, 1963, and "Polymer Handbook," H. Yasuda, and V. Stannett, John Wiley and Sons (Interscience Division), New York, III-229-240, 1975) and serves as a guide to the current capabilities of overwrap packaging film water vapor permeability.

TABLE I

| Film | Thickness* | Water Vapor Permeability** |
|---|---|---|
| Low density polyethylene | .0022 | 7.3 |
| High density polyethylene | .0045 | 35 |
| Polyvinylidene chloride (Saran) | .0025 | 0.05 |
| Polyacrylonitrile | N.A. | 30 |
| Cellulose acetate (unplasticized) | N.A. | 680 |
| Polystyrene | N.A. | 120 |
| Ethyl cellulose | N.A. | 1200 |

*thickness in inches
**units $[cm^3(STP)cm^{-2}sec^{-1}(cmHg)^{-1}cm \times 10^{-9}]$ In the above table, while exemplary film thicknesses are given for illustration of typical use film thickness, the water vapor permeability values are intrinsic to the materials and independent of thickness.

Also for purposes of illustration, examples of several edible films not within the scope of the present invention comprising ordinary shellac, cellulose derivatives and/or simple mixtures thereof and other currently available food approved film formers or coatings are listed on Table 2 along with their water vapor permeability constants as determined by methodology outlined in ASTM E96-66 (Reapproved 1972).

TABLE II

| Film | Thickness* | Water Vapor Permeability** |
|---|---|---|
| Hydroxypropyl methyl cellulose | .002 | 49,280 |
| Hydroxypropyl cellulose | .002 | 873 |
| Zein-Corn protein | .0004 | 168 |
| Paraffin wax on citrus fruit[A,B] | .0011 | 10 |
| Shellac-bleached | .0005 | 90 |
| Shellac-unbleached | .0012 | 81 |

*thickness in inches
**units $[cm^3(STP)cm^{-2}sec^{-1}(cmHg)^{-1}cm \times 10^{-9}]$
[A]use limited by Code of Federal Regulations (CFR) Vol. 21, 172.275, 1984.
[B]W. M. Miller and W. Grierson, Transactions of the ASAE, 1884-1887, 1983.

Ordinary shellac and cellulose derivatives are being used increasingly as a glaze in the pharmaceutical and confectionery industries. These food grade shellacs and/or cellulose derivatives are dissolved in ethyl alcohol and used for coating tablets and confections by panning, spraying, brushing or curtain coating methods. However, pure cellulose derivatives generally are poor coatings as they impart a lubrious texture when dissolving, exhibit minimal flexibility and generally poor water impermeable coatings.

Additionally, known coating compositions based upon pure, non-heat cured shellac suffer from other disadvantages. Noticeable off-flavors can be associated with shellac. While these problems are of less concern in the fabrication of orally administered medicines or vitamins, such problems are significant in other types of food products. Additionally, while known shellac based coatings initially offer good moisture impermeability, such coatings tend to swell in the presence of moisture over time. As the coatings swell and absorb moisture, their barrier properties deteriorate. Thus, there is a continuing need for improved shellac based coating compositions with extended shelf life due to decreased susceptibility to swelling in the presence of moisture. Accordingly, it is an object of the present invention to provide edible coating compositions with improved moisture impermeability.

It is a further object to provide coating compositions having improved resistance to water swelling.

Another object of the present invention is to provide coating compositions which contain neither non-food approved ingredients nor metal salts of fatty acids.

Still another object is to provide methods for preparing such coating compositions.

It is an obJect of the present invention to provide methods for preparing such coating compositions which can be used with heat-sensitive substrates.

It is a further object of the present invention to provide coating compositions having improved flavor due to masking of the off-flavors associated with shellac.

It has been surprisingly discovered that the above obJects can be realized and superior coating compositions and coatings obtained from cross-linked mixtures of shellac and certain edible reactants. In its principal method aspect, the present invention resides in the surprising discovery that coated articles, even heat sensitive articles, can be obtained with edible barriers exhibiting superior resistance to moisture migration using the instant coating compositions.

SUMMARY OF THE INVENTION

The present invention relates to coating compositions, to coatings prepared therefrom, to both pre-application and post-application methods of preparation, and to coated articles fabricated from the compositions. The coated compositions are based upon heat cured or polymerized shellac. In highly preferred embodiments, the shellac is heat cured or co-polymerized with certain edible members oontalning reactive hydroxyl or acid moieties and provide superior coatings or barriers to moisture and oxygen penetration as well as improved resistance to moisture swelling.

The coating compositions essentially comprise a heat cured mixture of a particularly defined shellac alone or in combination with a second edible reactant member. The edible reactant member can be selected from the group consisting of edible sources of polyphenolics, edible sources of benzaldehyde and its derivatives, acetylated monoglycerides, polyglycerol esters, straight chain mono-carboxylic acids, monoglycerides, diacetyl tartaric acid esters of monoglycerides and mixtures thereof. The ratio of shellac to reactant member essentially ranges from 1:0.001 to 1:1.5. In more preferred embodiments, the coatings additionally comprise an acid catalyst. Suitable acid catalysts include citric, malic, hydrochloric and tartaric acids. The ratio of acid catalyst to combined weight of shellac and reactants ranges from about 10 to 400:1.

The preferred method for preparing the coating compositions involves firstly dry blending the ingredients. Next, the blend is heated in a dry state to 130° to 175° C. for a period of 1 to 15 minutes. While molten, the heat cured composition so formed is dissolved in a food grade solvent. The solution is then applied to a substrate and the coated substrate is allowed to dry to form articles comprising the coatings of the present invention.

In another embodiment, the coated food articles of the present invention can be prepared by applying the reactants including an acid catalyst to a food substrate, preferably diluted in a food grade solvent and thereafter being dried at elevated temperatures to form a film. The film can range from 0.1 to 5 mil in thickness.

BRIEF DESCRIPTION OF THE DRAWING

The drawing is a table showing the results of testing of the water resistance of films prepared from the present coating compositions which results are further described with respect to Example 22.

DETAILED DESCRIPTION OF THE INVENTION

The present invention relates to edible coating compositions, to their methods of preparation, and to coated food products and to dry blends of unreacted materials useful in preparing the present coating compositions. The coating compositions essentially comprise a shellac, specially defined polymerized alone or in combination with certain edible reactant members having reactive hydroxyl or acid moieties. The present compositions are co-polymers wherein one monomer is shellac while a second monomer or reactant member can be selected from among several classes of materials. Each of these essential and preferred components as well as product preparation and use are described in detail below.

Throughout the specification and claims, percentages and ratios are by weight and temperatures in degrees Fahrenheit, unless otherwise indicated. Molecular weights are weight average molecular weights ($M_w$), unless otherwise indicated.

First Reactant

Shellac

A particular shellac is the essential material from which the present coating compositions are prepared. Shellac essentially comprises about 25% to 100% of the coating compositions. Better results in terms of both low moisture permeability and film flexibility are obtained when the shellac comprises about 50% to 99.9% of the composition. Best results are obtained when the shellac comprises about 58% to 99.9% of the coating composition.

Shellac or lac is a naturally occurring resin of animal origin. The chemical nature of shellac is still not completely understood. It is known that shellac is a polyester type of resin formed as a natural condensation product of aleuritic acid (9, 10, 16—trihydroxy palmitic acid) and schellolic acid. It has free carboxyl, hydroxyl and aldehyde groups and is unsaturated. When considering the properties of shellac, it must be remembered that shellac is a natural product of animal origin and differs somewhat from one source to another whether from India, Thailand or other areas.

Generally, however, shellac contains about 67.9% carbon, 9.1% hydrogen and 23.0% oxygen, corresponding to an emperical formula of $(C_4H_6O)_n$. Investigations into the molecular weight of fresh or unreacted shellac have concluded it to be about 1000. Based on this, the average shellac molecule has an average of $n=15$, and ranges from $n=6$ to $n=22$ (as described by W. H. Gardner, W. F. Whitmore, and H. J. Harris, Ind. Eng. Chem. 25,696(1933) and S. Basu, J. Indian Chem. Soc. 25,103(1948). The average molecule contains one free acid group, three ester linkages, five hydroxyl groups and possibly a free or potential aldehyde group as indicated by acid value, hydroxyl values, saponification value and carboxyl value determinations. Due to these groups and its chemical nature, shellac is known to age or polymerize with itself. Uncontrolled polymerization makes a shellac film less alcohol soluble and water permeable, but also undesireably increases the brittleness of a shellac film and lessens its usefulness as a coating.

Additionally, shellacs are commonly treated in various ways to modify its properties. Not all shellacs used in other food applications can be used herein. It is essential to use only dewaxed, filtered, carbon black decolorized, non-chemically modified or "virgin" shellac. It has been surprisingly found that other refined or bleached shellacs do not possess the reactivity required to cross-link so as to be useful in the present invention. Suitable shellacs are available from commercial suppliers such as Kane International, Larchmont, New York. Shellac can be reacted with the to be described reactants within a broad range. Useful weight ratios of shellac to second reactant(s) range from about 1:0.001 to 1:2. Better results in terms of permeability reduction, flexibility and water resistivity are obtained when the shellac to second reactant ranges from 1:0.001 to 0.25. Of course, the properries of the film materials which comprise the present compositions will vary somewhat with regard to specific values of water impermeability, flexibility, and the like depending upon selection of specific reactant materials or mixtures thereof and particular ratios between the reactants. However, especially with higher ratios of reactants with shellacs, minor amounts of the second reactant may not completely react with the shellac or even, with certain reactants, exhibit some self cross linking.

Indeed, while the present invention is directed primarily to the superior coating compositions which are copolymers of the present, particularly defined shellac and a second reactant member, the skilled artisan will appreciate that useful coating compositions can be prepared which are monomeric polymers using the selected shellacs described above alone.

Second Reactant

In one embodiment of the present invention, the present compositions and methods for their preparation essentially comprise a second edible reactant member.

The second reactant can be selected from any one of the several to-be described classes of materials. Each of these classes of materials have in common the presence of species having a reactive acid or hydroxy moiety which can inter-react with the reactive moieties of shellac. The present coating compositions can comprise from about 0 to 75% of the second reactant. For better results, the coating compositions comprise about 0.1% to 50%.

Organic Acid

The most highly preferred class of materials which can be used as the second reactant to prepare the copolymer coating compositions is certain mono- and di-carboxylic organic acids. Among the important benefits from employing the instant organic acid adducts is that the adduct or second reactants modestly increase the moisture impermeability of the films. Improvements in film flexibility are also obtained. Film flexibility is important to avoiding cracks and fissures in the film occasioned by handling or temperature change which can result in film failure. Additionally, the organic acids in part help mask off-flavors associated with shellac.

Especially useful herein are all edible non-substituted mono- and di-carboxylic acids. The skilled artisan will have no problem selecting particular acids for use herein. Preferred reactant materials due to their cost, flavor, availability and favorable affect on film flexibility, water durability and permeability are selected from the group consisting of adipic acid, succinic acid, oleic acid, lauric acid, stearic acid and mixtures thereof. Preferred for use herein are stearic acid, lauric acid, adipic acid and mixtures thereof.

Edible Sources of Polyphenolics

A second class of materials useful herein as a second reactant is edible source of polyphenolics. Any of a variety of common edible food approved materials can be employed as sources of polyphenolics and/or polyhydric alcohols. These materials can, for example, include plant parts, dehydrated fluid or solid extract or juices or concentrates, oils, gums, balsams, resins, oleoresins, waxes and distillates. Each material can be used alone or in combination with other edible sources of polyphenolic, tannins; both hydrolyzable and condensed, and/or polyhydric alcohols. Exemplary of the wide variety of known edible sources of polyphenolics and/or polyhydric alcohols are cranberries, hexane extracts of blanched or raw cashew nut meats, cassia pulp, grape skins, grape pulps, tea, coffee, hops, carob seeds and pods, soybeans, green apples, persimmons, tobacco and sorghum bran. A very large number of natural sources of polyphenols and tannins is given in D. K. Salunkhe, S. J. Jadhav, S. S. Kadam, J. K. Cheven, "Chemical, Biochemical, and Biologicl Significance of Polyphenols in Cereals and Legumes", CRC Handbook: Critical Reviews in Foods and Nutrition, Vol. 17, Issue 3, pp 277–305, (1982) and N. R. Reddy, M. D. Pierson, S. K. Sathe, D. K. Salunkhe, "Dry Bean Tannins: A Review of Nutritional Implications," Journal American Oil Chemists Society, Vol. 62, 3, 541–549, March 1985.

Edible Sources of Benzaldehydes and Benzaldehyde Derivatives

Another class of materials useful herein as a second reactant is edible sources of benzaldehydes and its derivatives. Any of a variety of common edible food approved materials can be employed as sources of benzaldehydes and/or benzaldehyde derivatives. These materials can, for example, include plant parts, dehydrated fluid or solid extracts or juices or concentrates, oils, gums, balsams, resins, oleoresin, waxes and distillates. Each can be used alone or in combination with other edible benzaldehydes and/or benzaldehyde derivatives. Exemplary of the wide variety of known edible sources of benzaldehyde and/or benzaldehyde derivatives are almonds and other nut meats, fruit pits such as prune, peach, apricot, cherry, plum or the like, cloves, vanilla beans, vanillin, anise, and numerous natural flavoring substances and/or synethetic flavoring substances such as vanillin, ethyl vanillin, anisaldehyde and the like.

Souces of Polyglycerol Esters

Polyglycerol esters ("PGE's") can also be used as the second reactant member. PGE's are widely used in the food art primarily as emulsifiers and are well known to the food product artisan. Polyglycerol esters in the appropriate form (oils, distillates, solids, etc.) are used alone or in combination with other edible polyglycerol esters. The polyglycerol esters of fatty acids up to and including the decaglycerol esters are prepared from corn oil, cottonseed oil, lard, palm oil from fruit, peanut oil, safflower oil, sesame oil, soybean oil, and tallow and the fatty acids derived from these substances (hydrogenated and non-hydrogenated) and/or oleic acid derived from tallow oil fatty acids, and/or the fatty acids derived from butter oil.

Sources of Acetylated Monoglycerides

Acetylated monoglycerides are widely used in the food art as emulsifiers. Common edible food approved sources of acetylated monoglycerides in any form (oils, solid, waxes, m.p. 5° C.–40° C.) can be used alone or in combination with other edible acetylated monoglycerides. The edible food approved acetylated monoglycerides are prepared by the interesterification of edible fats with triacetin and in the presence of catalytic agents that are not food additives or are not authorized regulated additives, followed by a molecular distillation or by steam stripping; or by the direct acetylation of edible monoglycerides with acetic anhydride without the use of catalyst or molecular distillation and with the removal by vacuum distillation, if necessary, of the acetic acid, acetic anhydride and triacetin.

Sources of Stearoyl-2-lactylates and Lactylic Esters of Fatty Acids

Edible food approved sources of stearoyl-2-lactylate are prepared by the reaction of stearic acid and lactic acid and conversion to the sodium or calcium salts. The lactylic esters of fatty acids are prepared from lactic acid and fatty acids and/or oleic acid derived from tall oil fatty acids. Each of these composition types can be used as the second reactant member.

Sources of Carboxylic Acids

Common edible food approved sources of straight chain monobasic carboxylic acids and their associated fatty acids can be used herein as the second reactant member. These materials are manufactured from fats and oils derived from edible sources. The edible acids are capric, caprylic, lauric, myristic, oleic, palmitic, and stearic acids as well as margaric, arachidic, behenic and lignoceric acids.

Sources for natural edible food approved di- and tri-carboxylic acids include fruit and citrus peel, pulp, juices; also, citric acid solvent extraction from conventional *Aspergillus niger* fermentation liquor, and numerous other natural sources.

Sources for di- and tri-carboxylic acids manufactured by synthetic means are also acceptable provided the FDA-CFR written regulations are practiced as to source and method of preparation.

Mono- and di-glyceride

Mono- and di-glycerides can each be used as the second reactant member. Edible food approved monoglycerides are prepared by the esterification of fatty acids, consisting of one or any mixture of the following straight chain monobasic carboxylic acids and their associated fatty acids manufactured from fats and oils derived from edible sources: capric, caprylic, lauric, myristic, oleic, palmitic and stearic acids, and glycerol. The resulting product is a mixture of mono- and di-glycerides and can be used as such as well as the distilled monoglycerides of fatty acids and combinations thereof.

Sources of Diacetyl Tartaric Acid Esters of Monoglycerides (DATEMS)

Edible food approved diacetyl tartaric acid esters of monoglycerides (DATEMS) are obtained by reacting a monoglyceride (preferably molecularly disrilled) and diacetyl tartaric acid anhydride. The physical properties of the DATEMS depend primarily on the type of fatty acids and the molar quantities involved. Generally, the DATEMS are liquid and/or solids at room temperature (mp. 0°–50° C.).

Optional Ingredients

A variety of optional ingredients can be added to the present compositions to improve one or more properties. Such adjuvants can include, for example, flavors, colors, vitamins and the like. Additionally, additives which reduce the growth of microorganisms can be incorporated into the described coating compositions especially when the compositions are to be used for providing protective films on external surfaces. Such additives or preservatives include sorbic acid, potassium sorbate, methyl p-hydroxybenzoate, sodium benzoate, sodium propionate, and propyl p-hydroxylbenzoate. The addition of even small concentrations of such preservatives results in a marked improvement in reducing or preventing the growth of microorganisms. Adequate protection against the growth of microorganisms is obtained if the concentration of the preservative in the coating constitutes about 0.01% to 0.2% by weight of the coating. In addition, suitable anti-oxidants approved for food use can be included in the coating compositions.

Method of Preparation

The present coating compositions can be obtained by blending the unreacted components and heat curing in a dry state. The heat curing can be practiced as convenient either before or after application to the desired substrate. The blending can be done either by dry blending or by dissolving in a solvent and thereafter removing the solvent. The process of this invention produces a chemical union between all of the reactants with the shellac forming an integral part of the resulting resinous molecules.

The most highly preferred method is the preapplication curing embodiment. This method is preferred due to the realization of films which are more highly water-impermeable and resistant to water swelling. The shellac alone if used by itself, or if along with the other materials, all the components are first dry blended to form a homogeneous mixture. If desired, such formulated unreacted compositions can themselves be marketed on a supplier basis. The order in which the components are admixed is not critical. Thereafter, the dry blend is heated to about 130° to 175° C., preferably 138° to 150° C. for a period of about 1 to 15 minutes to form the present heat cured coating compositions. Temperatures in excess of 175° C. or addition of acid catalysts (organic or mineral) cause too rapid and uncontrollable polymerization with the resulting material being insoluble in ethanol and other food approved solvents.

While still molten, the melt or magma is poured into a room temperature food grade solvent such as ethanol with agitation. If allowed to cool to solidification, the heat cured shellac is not readily soluble. However, if desired, the cured shellac may be allowed to solidify and then be reheated as convenient for dissolution into the solvent.

An acid catalyst is undesirable in this embodiment of the method of preparation in contrast to the to-be-described post application curing technique. Indeed, excessive acidity can cause the reaction to proceed at an uncontrolled rate resulting in an unusable reaction product and thus desirably the dry mixture is substantially free of an acid catalyst. In the undiluted form, the shellac itself has sufficient acidic character to initiate polymerization at a controllable rate upon simple heating.

Within these reaction parameters, it is desired to produce cross-linked shellac or copolymer having a weight average molecular weight ($M_w$) ranging from about 1,500 to 6,000 as determined by gel permeation chromatography. These pre-application curing methods are particularly useful when coatings are desired to be applied to heat sensitive materials, e.g., materials of low melting point ingredients and having particular shapes, e.g., chocolate chips. The solution may also be removed to provide resins for the coating compositions.

The coating compositions realized herein are thermoplastic resins. The resin compositions thus can be used for curtain-coating techniques of food coating, i.e., involving the extrusion of a sheet which is placed over the substrate with the aid of suction while still molten. The described resin coating compositions, however, are particularly suitable for use in conventional coating techniques such as dipping, brushing or spraying. These operations can be conducted employing a melt of the coating composition or by employing solutions thereof in food grade solvents.

Another suitable method of preparation is to heat cure after application to a substrate of the reactant material(s). In this embodiment, the shellac and/or other components including acid catalyst are dissolved in a food grade solvent, e.g., ethanol, to form preferably about a 10% to 20% solution which concentration includes an acid catalyst. Among food grade solvents, ethanol is the solvent of choice.

Shellacs are not generally readily soluble in water. However, certain ammonia treated shellacs are more easily dissolved in water. Also, when water is sweetened with ammonia to a pH of 8.5 to 9.0, the present, particularly defined shellacs can be dissolved in the water. Modest additions of alcohol to water can be used, if desired, to disperse the mono- and di-carboxylic acid materials in the alkaline water if employed. The aqueous solution can be applied to a substrate and allowed to dry to form a film. If alkaline water is used as the solvent, then thereafter, a second solution containing the acid catalyst can be applied over the dried film of unreacted reactants. Increased amounts of acid catalyst should be employed so as to first neutralize the residual alkalinity. Thereafter, the coated substrate can be heat treated as described further below.

An edible strong acid catalyst is essentially employed in this embodiment of forming the present coating compositions. The acid catalyst allows for the accelerated and controlled cross-linking of the shellac. Suitable for use herein are both edible mineral and organic acids. The useful organic acid catalyst herein are distinguished from the above described adduct organic acid reactants principally by the relatively greater acidity of the present strong acid catalyst materials. Exemplary materials useful herein for the acid catalyst includes citric acid, tartaric acid, phosphoric, hydrochloric acid, malic acid and mixtures thereof. Preferred for use herein are citric acid and hydrochloric acid.

The acids are used in amounts effective to promote and accelerate the cross-linking of the shellac. Since the cross-linking step is practiced in a dry state, conventional pH measurements of acidity are inappropriate. However, good results are obtained when the weight ratio of acid catalyst to the weight of shellac in the dry composition ranges from about 0.001 to 0.1:1. Thus, if ethanol is the solvent, the reactant solutions from which the pre-heat cured films are prepared can contain about 0.1% to 10% of the acid catalyst member(s) and preferably 0.25% to 5.0% in addition to the concentrations of shellac if used alone, or if used in combination with a second reactant. Best results in terms of optimum hardness and permeability are obtained when the solution concentration ranges from 0.5% to 3%.

The solution is then applied by conventional techniques to a substrate to form a coated substrate and dried. The dried, coated substrate is then heated for about 2 to 15 minutes at 130° to 180° C. to cure the coated composition. Slightly longer heating times may be required to bring the temperature to within the above temperature range if the coated substrate has not been completely dried prior to heating. After the heat curing step, the substrate will be covered with the coatings of the present invention. This embodiment is particularly useful for use with substrates which are heat tolerant, e.g., baked goods or container materials.

Of course, additional coat layers, e.g., second or even fifth, can be applied to the substrate if desired to increase further the sealing properties of the coat. The coating obtained with the described coating compositions are strong, highly water and oxygen impermeable, resistant to swelling, flexible and resilient even at freezer temperatures even in the form of thin films. Continuous, pin-hole-free coatings are readily obtained.

The optimum thickness of a coating employing the present compositions will vary depending on the particular application involved, the degree of protection desired, and the expected storage environment. As a general rule, the coating should have sufficient thickness to assure a continuous coating and give the desired degree of protection, and whether or not it is desirable for the barrier not to be readily apparent. Good sealing protection can be achieved with a coating thickness as thin as 0.1 mil. Greater protection, while nonetheless being organoleptically acceptable, can be provided by films up to about 5 mil in thickness. Preferred thicknesses range from about 0.25 to 2 mil.

The coating compositions can be used on all manner of substrates used in connection with food products whether non-edible, e.g., on containers, sticks and the like, or edible substrates, e.g., fruits, vegetables, meats, candies, tablets for oral use and the like. The present coating compositions find particular usefulness as barriers in composite food products having a first food phase or region of one material and a second phase or region of a second material. For example, pieces of soft, moist cheese may be coated with the present film coat and sandwiched between dry cracker slices to provide conventionally packaged snacks which are not subject to staling as quickly by moisture migration or other interaction between the cheese and cracker. Surprisingly, the present coatings find even greater usefulness with high moisture, frozen or chilled food products such as ice cream sandwiches or cookies and fruit (both pieces and jams, jellies and preserves) or chocolate chips and dairy products.

The claims and the specification describe the invention presented, and the terms that are employed in the claims draw their meaning from the use of such terms in the specification. Some terms employed in the prior art may be broader in meaning than specifically employed herein. Whenever there is a question between the broader definition of such term as used in the prior art and the more specific use of the term herein, the more specific meaning is meant.

The invention is further illustrated by the following examples.

EXAMPLE 1

Forty grams of dewaxed, carbon filtered shellac and 5.0 grams of stearic acid were dissolved in 200 ml 95% ethanol and warmed slightly to about 125° F. to effect solution with stirring. Upon complete solution, 5 ml of a concentrated citric acid solution (35 g in 80 ml 95% ethanol) was added. The solution was spread on teflon, glass and vegetable paper substrates and heat cured at 300° F. (150° C.) for 10 minutes. The resulting film was water resistant, exhibited no water swelling and no stess cracking when flexed. The coating was tough, abrasion resistant and visibly free from defects.

EXAMPLE 2

Forty grams of dewaxed, carbon filtered shellac and 2.1 grams of succinic acid were dissolved in 200 ml 95% ethanol and warmed slightly to about 125° F. to effect solution with stirring. Upon complete solution, 0.2 grams concentrated HCl in 10 ml 95% ethanol was added. The solution was spread on teflon, glass and vegetable paper substates and heat cured at 300° F. (150° C.) for 10 minutes. The resulting film was wear resistant, exhibited no water swelling and no stress cracking when flexed. The coating was abrasion resistant, tough and visibly free from defects.

EXAMPLE 3

Forty grams of dewaxed, carbon filtered shellac and 14.1 grams of lauric acid were dissolved in 200 ml of 95% ethanol and warmed slightly to about 125° F. (51° C.) to effect solution with stirring. Upon complete solution, 5 ml of a concentrated citric acid solution (35 g in 80 ml 95% ethanol) was added. The solution was spread on one-half of a baked sugar wafer and heat cured at 300° F. (150° C.) for 10 minutes. The resultant treated half wafer appeared glazed and possessed a tough hard coating, the untreated half wafer appeared normal in every respect—no glaze and no tough hard coating. Small water droplets were placed on both the treated and untreated wafer. The droplets on the unteated surface ingressed immediately into the wafer substrate with subsequent softening of the wafer, while the treated surface droplets evaporated (about 10+ minutes) before any degradation of the resultant coating was evident. The coating on the wafer gave no off taste with respect to the untreated side and also exhibited significant moisture resistance.

EXAMPLE 4

Forty grams of dewaxed, carbon filtered shellac and 5.0 grams of stearic acid were placed in an oil jacketed heating vessel along with 5 ml of a concentrated citric acid solution (35 g in 80 ml 95% ethanol) and heated to 135° C. The magma or molten mixture immediately stiffened, became unstirrable, and would not disolve into a 10:1 mixture of ethanol (95%) and ethylacetate.

EXAMPLE 5

Forty grams of dewaxed, carbon filtered shellac and 12.5 grams of stearic acid were placed in an oil Jacketed heating vessel and heated to 135° C. Upon reaching temperature the magma began to foam and the reaction was run for eight minutes with stirring. The magma or molten mixture was somewhat fluid with a final temperature of 140° C. The molten mixture was poured into 900 ml of a 10:1 mixture of 95% ethanol and ethylacetae with high shear mixing and upon solution was diluted to one liter. The resulting film was hard, glossy, continuous, abrasion and water resistant.

EXAMPLE 6

One hundred grams ot dewaxed, carbon filtered shellac and 2.7 grams of decaglycerol monooleate were placed in an oil jacketed heating vessel and heated to 138° C. The reaction was run for 7.5 minutes with stirring. The magma or molten material was stiff with a final temperature of 148° C. The molten material was poured into 900 ml of a 10:1 mixture of 95% ethanol and ethylacetate with high shear mixing and upon solution was diluted to one liter.

EXAMPLE 7

One hundred grams of dewaxed, carbon filtered shellac and 3.4 grams of vanillin were placed in an oil jacketed heating vessel and heated to 138° C. Upon reaching temperature the magma or molten mixture began to foam and the reaction was run for seven minutes with stirring. The magma was somewhat stiff with a final temperature of 147° C. The molten mixture was poured into 900 ml of a 10:1 mixture of 95% ethanol and ethylacetate with high shear mixing and upon solution was diluted to one liter.

EXAMPLE 8

One hundred grams of dewaxed, carbon filtered shellac and 5.0 grams of acetylated monoglycerides (90-100% acetylated) were placed in an oil jacketed heating vessel and heated to 138° C. Upon reaching temperature the magma or molten mixture began to foam and the reaction was run for 7.5 minutes with stirring. The magma was stiff with a final temperature of 148° C. The molten mixture was poured into 900 ml of a 10:1 mixture of 95% ethanol and ethylacetate with high shear mixing and upon solution was diluted to one liter.

EXAMPLE 9

1080 grams of dewaxed, carbon filtered shellac and 120 grams of stearic acid were placed in an oil jacketed heating vessel and heated to 135° C. Upon reaching temperature the magma or molten mixture began to foam and the reaction was run for eight minutes with stirring. The magma was somewhat fluid with a final temperature of 142° C. The molten mixture was poured into 900 ml of a 10:1 mixture of 95% ethanol and ethylacetate with high shear mixing and upon solution was diluted to one liter.

EXAMPLE 10

One hundred grams of dewaxed, carbon filtered shellac and 3.4 grams of tannic acid were placed in an oil jacketed heating vessel and heated to 138° C. Upon reaching temperature the magma or molten mixture began to foam and the reaction was run for eight minutes with stirring. The magma was stiff and grainy with a final temperature of 147° C. The molten mixture was poured into 900 ml of a 10:1 mixture of 95% ethanol and ethylacetate with high shear mixing and upon solution was diluted to one liter.

EXAMPLE 11

One hundred grams of dewaxed, carbon filtered shellac and 3.7 grams of anisaldehyde were placed in an oil jacketed heating vessel and heated to 135° C. Upon reaching temperature the magma or molten mixture began to foam and the reaction was run for nine minutes with stirring. The magma was soft and fluid with a final temperature of 148° C. The molten mixture was poured into 900 ml of a 10:1 mixture of 95% ethanol and ethylacetate with high shear mixing and upon solution was diluted to one liter.

EXAMPLE 12

One hundred grams of dewaxed, carbon filtered shellac and 3.2 grams of oleic acid were placed in an oil jacketed heating vessel and heated to 140° C. Upon reaching temperature the magma or molten mixture began to foam and the reaction was run for 8.5 minutes with stirring. The magma was soft and fluid with a final temperature of 148° C. The molten mixture was poured into 900 ml of a 10:1 mixture of 95% ethanol and ethylacetate with high shear mixing and upon solution was diluted to one liter.

EXAMPLE 13

One hundred grams of dewaxed, carbon filtered shellac and 1.3 grams of stearic acid were placed in an oil jacketed heating vessel and heated to 140° C. Upon reaching temperature the magma or molten mixture began to foam and the reaction was run for 8.5 minutes with stirring. The magma was moderately soft and fluid with a final temperature of 148° C. The molten mixture was poured into 900 ml of a 10:1 mixture of 95% ethanol and ethylacetate with high shear mixing and upon solution was diluted to one liter.

EXAMPLE 14

One hundred grams of dewaxed, carbon filtered shellac was placed in an oil jacketed heating vessel and heated to 140° C. Upon reaching temperature the magma or molten mixture began to foam and the reaction was run for eight minutes with stirring. The magma was stiff and flowable with a final temperature of 150° C. The molten mixture was poured into 900 ml of a 10:1 mixture of 95% ethanol and ethylacetate with high shear mixing and upon solution was diluted to one liter.

EXAMPLE 15

One hundred grams of dewaxed, carbon filtered shellac and 3.3 grams of tartaric acid were placed in an oil jacketed heating vessel and heated to 138° C. Upon reaching temperature the magma or molten mixture began to foam and the reaction was run for eight minutes with stirring. The magma was grainy and stiff with a final temperature of 148° C. The molten mixture was poured into 900 ml of a 10:1 mixture of 95% ethanol and ethylacetate with high shear mixing and upon solution was diluted to one liter.

EXAMPLE 16

One hundred grams of dewaxed, carbon filtered shellac and 3.3 grams of succinic acid were placed in an oil jacketed heating vessel and heated to 140° C. Upon reaching temperature the magma or molten mixture began to foam and the reaction was run for 8.5 minutes with stirring. The magma was moderately stiff with a final temperature of 148° C. The molten mixture was poured into 900 ml of a 10:1 mixture of 95% ethanol and ethylacetate with high shear mixing and upon solution was diluted to one liter.

EXAMPLE 17

One hundred grams of dewaxed, carbon filtered shellac and 4.1 grams of distilled monoglycerides were placed in an oil jacketed heating vessel and heated to 138° C. Upon reaching temperature the magma or molten mixture began to foam and the reaction was run for 8.5 minutes with stirring. The magma was soft and flowable with a final temperature of 148° C. The molten mixture was poured into 900 ml of a 10:1 mixture of 95% ethanol and ethylacetate with high shear mixing and upon solution was diluted to one liter.

EXAMPLE 18

One hundred grams of dewaxed, carbon filtered shellac and 3.6 grams of diacetyl tartaric acid esters of monoglycerides were placed in an oil jacketed heating vessel and heated to 138° C. Upon reaching temperature the magma or molten mixture began to foam and the reaction was run for nine minutes with stirring. The magma was moderately stiff with a final temperature of 147° C. The molten mixture was poured into 900 ml of a 10:1 mixture of 95% ethanol and ethylacetate with high shear mixing and upon solution was diluted to one liter.

EXAMPLE 19

One hundred grams of dewaxed, carbon filtered shellac and 3.2 grams of stearoyl-2-lactylate were placed in an oil jacketed heating vessel and heated to 138° C. Upon reaching temperature the magma or molten mixture began to foam and the reaction was run for nine minutes with stirring. The magma was moderately stiff with a final temperature of 147° C. The molten mixture was poured into 900 ml of a 10:1 mixture of 95% ethanol and ethylacetate with high shear mixing and upon solution was diluted to one liter.

EXAMPLE 20

Forty grams of dewaxed, carbon filtered shellac and 56.5 grams of lauric acid were placed in an oil jacketed heating vessel and heated to 135° C. Upon reaching temperature the magma or molten mixture began to foam and the reaction was run for fifteen minutes with stirring. The magma was fluid and pourable with a final temperature of 148° C. The molten mixture was poured into 900 ml of a 10:1 mixture of 95% ethanol and ethylacetate with high shear mixing and upon solution was diluted to one liter.

EXAMPLE 21

One hundred grams of dewaxed, carbon filtered shellac and 25.8 grams of cranberry concentrate were placed in an oil jacketed heating vessel and heated to 138° C. Upon reaching temperature the magma or molten mixture began to foam and the reaction was run for nine minutes with stirring. The magma was soft and fluid with a final temperature of 146° C. The molten mixture was poured into 900 ml of a 10:1 mixture of 95% ethanol and ethylacetate with high shear mixing and upon solution was diluted to one liter.

EXAMPLE 22

One hundred grams of dewaxed, carbon filtered shellac and 5.6 grams of cashew nut oil-hepane extract were placed in an oil jacketed heating vessel and heated to 137° C. Upon reaching temperature the magma or molten mixture began to foam and the reaction was run for nine minutes with stirring. The magma was moderately hard and fluid with a final temperature of 149° C. The molten mixture was poured into 900 of a 10:1 mixture of 95% ethenol and ethylacetate with high shear mixing and upon solution was diluted to one liter.

The water vapor permeabilities of the edible films prepared as in the above examples as well as pure unheat cured shellac have the values provided in Table III as follows:

TABLE III
WATER VAPOR PERMEABILITIES FOR SHELLAC FILMS

| FILM COMPOSITION | H$_2$O VAPOR PERMEABILITY* |
| --- | --- |
| shellac-unbleached-unreacted | 20 |
| Example | |
| 1 | 2.3 |
| 2 | 1.3 |
| 3 | N.A. |
| 4 | N.A. |
| 5 | 0.41 |
| 6 | 15.2 |
| 7 | 7.6 |
| 8 | 6.8 |
| 9 | 0.88 |
| 10 | 2.5 |
| 11 | 3.3 |
| 12 | 3.1 |
| 13 | 3.5 |
| 14 | 1.8 |
| 15 | 4.2 |
| 16 | 3.8 |
| 17 | 1.8 |
| 18 | 2.0 |
| 19 | 2.1 |
| 20 | 0.42 |
| 21 | 0.97 |
| 22 | 1.3 |

*cm$^3$(SPT)cm$^{-2}$sec$^{-1}$cmHg$^{-1}$cm × 10$^{-8}$

The values given in Table III above indicate that compared to untreated shellac the present films exhibit superior resistance to moistur®permeability.

The increased resistance of these prepared films as in the above example as well as bleached shellac to water swelling is provided in Table IV as follows:

TABLE IV

Detailed Description of the Drawing

The values given in Table IV indicate that when compared to conventional bleached shellac, the present films exhibit superior resistance to water swelling.

The increases in both weight average ($M_w$) and number average ($M_n$) molecular weights and the increased narrowness of the molecular weight distribution ($M_w/M_n$) of the prepared films in the examples as compared to the unheated shellac samples is evident as shown in Table V as follows:

TABLE V

FILM COATING MOLECULAR WEIGHT DISTRIBUTION[A]

| FILM COMPOSITION | $M_w$ | $M_n$ | $M_w/M_n$ | $M_z$ |
|---|---|---|---|---|
| Unreacted Shellac | | | | |
| Shellac 56 SONNE (pale) | 821 | 152 | 5.39 | 3083 |
| Shellac 58 KOMET (amber) | 1023 | 204 | 5.01 | 2824 |
| Shellac 60 PRIMA (orange) | 571 | 149 | 3.82 | 2269 |
| Example | | | | |
| 7 | 2639 | 1131 | 2.33 | 5999 |
| 8 | 3316 | 1419 | 2.33 | 7009 |
| 9 | 2168 | 1159 | 1.87 | 4356 |
| 10 | 3194 | 1205 | 2.65 | 14645 |
| 14 | 1910 | 961 | 1.99 | 4275 |
| 15 | 2867 | 1232 | 2.33 | 6786 |
| 18 | 1755 | 848 | 2.07 | 4391 |

$M_w$, weight average molecular weight;
$M_n$, number average molecular weight;
$M_w/M_n$, molecular weight distribution,
$M_z$, z average molecular weight;

[A]Determination using a Waters 150C ALC/GPC, m-cresol at 110° C. on a microstyragel columns (1.0E5, 1.0E4 and 1.0E3 Angstrom), flow rate 1.0 ml/min, 150 uL sample injection (0.05 g sample in 10.0 ml m-cresol). Data reduction using a Nelson Analytical Model 444 Chromatography Data System with a GPC software package. Standardized with a series of narrow dispersity anionically polymerized polystyrene standards (Waters Associates).

The effect of molecular weight or molecular weight distribution on polymer properties (as described by E. A. Collins, J. Bares, and F. W. Billmeyer, Jr., Experiments in Polymer Science, Wiley, New York, 1973 p. 312) are indicated in Table VI below.

TABLE VI

EFFECT OF MOLECULAR WEIGHT OR MOLECULAR WEIGHT DISTRIBUTION ON POLYMER PROPERTIES

| Polymer Properties | Increased Molecular Weight ($M_w$) | Narrow the Molecular Weight Distribution ($M_w/M_n$) |
|---|---|---|
| Tensile Strength | + | + |
| Elongation | + | − |
| Yield Strength | + | − |
| Toughness | + | + |
| Brittleness | + | − |
| Hardness | + | − |
| Abrasion Resistance | + | + |
| Softening Temperature | + | + |
| Melt Viscosity | + | + |
| Adhesion | − | − |
| Chemical Resistance | + | + |

TABLE VI-continued

EFFECT OF MOLECULAR WEIGHT OR MOLECULAR WEIGHT DISTRIBUTION ON POLYMER PROPERTIES

| Polymer Properties | Increased Molecular Weight ($M_w$) | Narrow the Molecular Weight Distribution ($M_w/M_n$) |
|---|---|---|
| Solubility | − | 0 |

+, property goes up
−, property goes down
0, little change

It is clearly evident that these above prepared films are superior in every desirable polymer property as supported by the data in Tables III and IV when compared to the untreated shellac films.

What is claimed is:

1. An edible coating polymer having a low water vapor permeability, comprising the heat cured reaction product of:
   a refined, carbon filtered, unbleached, edible, virgin shellac,
   and wherein the product has an average molecular weight ranging from bout 1,500 to 6,000

2. The edible coating composition of claim 1 wherein the shellac comprises about 25% to 99.5% by weight of the coating composition and additionally comprising:
   about 0.1% to 75% by weight of the composition of an edible member having a reactive hydroxyl or acid moiety selected from the group consisting of:
   a. edible sources of polyphenolics,
   b. edible sources of benzaldehyde derivatives,
   c. polyglycerol esters,
   d. edible mono- and di-carboxylic acids,
   e. acetylated monoglycerides,
   f. diacetyl tartaric acid esters of monoglycerides,
   g. lactylic esters of fatty acids,
   h. mono- and di-glycerides,
   and mixtures thereof.

3. The coating composition of claim 2 wherein the shellac comprises about 50% to 99.9% by weight of the coating composition.

4. The edible coating composition of claim 2 wherein the edible source of mono- or carboxylic acid is selected from the group consisting of succinic acid, oleic acid, lauric acid, stearic acid and mixtures thereof.

5. The edible coating composition of claim 3 wherein the shellac comprises about 58% to 99.9% of the coating composition.

6. The edible coating composition of claim 2, 3, or 5 wherein the edible member is an edible source of polyphenolics.

7. The edible coating composition of claim 2, 3, or 5 wherein the edible member is an edible source of benzaldehyde derivatives.

8. The edible coating composition of claim 2, 3, or 5 wherein the edible member is a polyglycerol ester.

9. The edible coating composition of claim 2, 3, or 5 wherein the edible member is an edible mono- or di-carboxylic acid.

10. The edible coating composition of claim 2, 3, or 5 wherein the edible member is an acetylated monoglyceride.

11. The edible coating composition of claim 2, 3, or 5 wherein the edible member is a lactylic ester of fatty acids.

12. The edible coating composition of claim 2, 3, or 5 wherein the edible member is a mono- or di-glyceride.

* * * * *

UNITED STATES PATENT AND TRADEMARK OFFICE
CERTIFICATE OF CORRECTION

PATENT NO. : 4,710,228
DATED : Dec. 1, 1987
INVENTOR(S) : Seaborne et al.

It is certified that error appears in the above-identified patent and that said Letters Patent are hereby corrected as shown below:

In the Abstract, next to last line, "fro" should be -- from --.

Col. 2, line 4 - "rhese" should be -- these --.
Col. 3, line 44 - "on" should be -- in --.
Col. 4, line 28 - "obJect" should be -- object --.
Col. 4, line 35 - "obJect" should be -- object --.
Col. 4, line 52 - "oontaining" should be -- containing --.
Col. 9, line 20 - "disrilled" should be -- distilled --.
Col. 13, line 18 - "Jacketed" should be -- jacketed --.
Col. 13, line 30 - "ot" should be -- of --.
Col. 16, line 28 - "900 of" should be -- 900 ml of --.
Col. 16, line 65 - "moistur ®permeability" should be -- moisture permeability --.
Col. 18, line 43 - "carboxylic" should be -- di-carboxylic --.
Col. 17, line 9 - "increases" should be -- increase --.
Col. 18, line 23 - "6,000" should be -- 6,000. --.

Signed and Sealed this

Fifteenth Day of November, 1988

Attest:

DONALD J. QUIGG

Attesting Officer

Commissioner of Patents and Trademarks